United States Patent [19]

Hernandez

[11] 4,100,922

[45] Jul. 18, 1978

[54] DISPOSABLE DIAPER

[75] Inventor: John Michael Hernandez, East Brunswick, N.J.

[73] Assignee: Colgate-Palmolive Company, New York, N.Y.

[21] Appl. No.: 594,345

[22] Filed: Jul. 9, 1975

[51] Int. Cl.² ............................................. A61F 13/16
[52] U.S. Cl. ................................................... 128/284
[58] Field of Search ............ 128/284, 287, 286, 290 R

[56] References Cited

U.S. PATENT DOCUMENTS

| | | | |
|---|---|---|---|
| 3,610,244 | 10/1971 | Jones, Sr. | 128/287 |
| 3,776,233 | 12/1973 | Schaar | 128/287 |
| 3,794,038 | 1/1974 | Buell | 128/287 |
| 3,884,234 | 5/1975 | Taylor | 128/287 |
| 3,913,578 | 10/1975 | Schaar | 128/287 |
| 3,924,626 | 12/1975 | Lee | 128/287 |
| 3,929,134 | 12/1975 | Karami | 128/284 |

*Primary Examiner*—Robert W. Michell
*Assistant Examiner*—Jerome D. Stremcha
*Attorney, Agent, or Firm*—Norman Blumenkopf; Herbert S. Sylvester; Murray M. Grill

[57] ABSTRACT

A disposable diaper substantially rectangular in shape and comprising in order, a water pervious layer or face sheet, an absorbent pad layer and a water impervious layer, said diaper having a pair of abutting, centrally located longitudinal panels defined by three substantially parallel longitudinal folds extending the length of said diaper. A flap portion is adjacent each of the panels. Adhesive means are positioned on each of the panels approximately centrally located longitudinally thereof for securing the longitudinal edges of the diaper in the crotch portion. The diaper in the folded condition has an "hour-glass" or "M" shaped configuration providing improved fit and particularly in the crotch area. The lateral edges of the diaper lie flat when the diaper is in open position, greatly facilitating manual manipulation of the diaper when applied to an infant. The diaper has significantly improved efficiency and appearance.

1 Claim, 2 Drawing Figures

DISPOSABLE DIAPER

BACKGROUND OF THE INVENTION

1. Field of the Invention

This invention relates generally to diapers and more particularly to an improved disposable diaper having a close, sealing fit in the crotch area without causing dicomfort to an infant clad therewith.

2. Description of the Prior Art

Conventional disposable diapers generally comprise in order, a rectangular back sheet of hydrophobic waterproof i.e., water impervious material, a rectangular absorbent pad serving as a waste fluid reservoir and a rectangular top or face sheet of water pervious, generally hydrophobic material. In general, the back sheet is somewhat larger, ie, its longitudinal edges extend beyond the longitudinal edges of the absorbent pad layer and the water pervious layer. Conventional disposable diapers are prepared according to one of a number of prefolded configurations, to provide a narrowed portion in the crotch area to improve fit, appearance and diaper performance such as absorptive capacity.

The diaper should possess sufficient strength and particularly resistance to tearing in the crotch area, where it is often subjected to the bulk of the stresses resultant upon physical activity of the diaper-clad infant. Conversely the diaper must be readily capable of being closely but comfortably fitted to the physical contour of the infant with a minimum of effort and inconvenience to the mother. Close fit is essential to create a seal to contain discharged waste fluids to thus allow the absorbent pad layer sufficient time to absorb the waste fluid.

According to one known diaper assembly structure, the flap portions of the back sheet or water impervious layer are folded around the longitudinal edges of the absorbent pad and secured to the face sheet by adhesive. This provides a uniform "double" thickness along the longitudinal edges of the diaper and thus enhances the strength and tear resistant properties of the diaper in this area. However, these diapers are rather cumbersome and awkward to apply. Moreover, the bulky nature of the diaper leads to local buckling and bulging of the back sheet away from the thighs and trunk of the infant with consequent loss of sealing contact.

Additionally, the "double" thickness portion of the diaper tends to significantly reduce the efficiency of air circulation thoroughut the diaper material. Heat dissipation is thus rendered highly inefficient, which can lead to infant discomfort, chaffing and heat rash, and the like. The problem is further aggravated since the folded-over portion of the back sheet is relatively large, thereby reducing the effective absorptive area of the diaper in the crotch portion. This can actually increase dripping of excess waste fluid.

Diapers folded in a box pleat configuration are also known. Generally, however, the panels defined by the box pleated diaper are spaced substantially from each other, requiring that the central panel behind the pleated panels receive most of the waste fluid. To provide the desired absorptive capacity, diapers of this construction sag away from the trunk of the body impairing proper utilization of the absorptive capabilities of the diaper.

Diapers of the aforedescribed type are generally provided with four longitudinal folds and are conventionally termed "wing-fold" diapers. Aside from certain objectionable performance characteristics, there diapers do not tend to lie flat a completely open position. This causes considerable problems when attempting to dress the infant since the diaper tends to bulge, bow, etc. making a close fit highly difficult.

OBJECTS OF THE INVENTION

A primary object of the present invention is to provide a disposable diaper wherein the foregoing disadvantages are eliminated or at least mitigated to a substantial extent.

Another object of the invention is to provide a disposable diaper which may be readily and conveniently manipulated to provide a close, comfortable fit in the crotch area.

Yet another object of the invention is to provide a disposable diaper wherein the lateral edges lie flat when the diaper is in open position.

Still another object of the invention is to provide a disposable diaper having improved strength and resistance to tear and especially in the crotch portion.

Yet another object of the invention is to provide a disposable diaper having improved performance characteristics and capable of maintaining the diaper-clad infant in a drier condition.

A further object of the invention is to provide a disposable diaper having improved appearance when applied to an infant.

Other objects and advantages will become more apparent as the description proceeds.

SUMMARY OF THE INVENTION

The foregoing and related objects are attained in accordance with the present invention which, in its broader aspects, provides a disposable diaper having four longitudinal sections defined by three substantially parallel longitudinal folds comprising a pair of abutting, centrally located longitudinal panels extending the length of the diaper, said panels being of approximately equal width, a flap portion adjacent each of said panels and adhesive means substantially centrally located longitudinally on each of said panels.

The invention is illustrated in the accompanying drawings wherein.

DETAILED DESCRIPTION OF THE INVENTION

Figure 1:
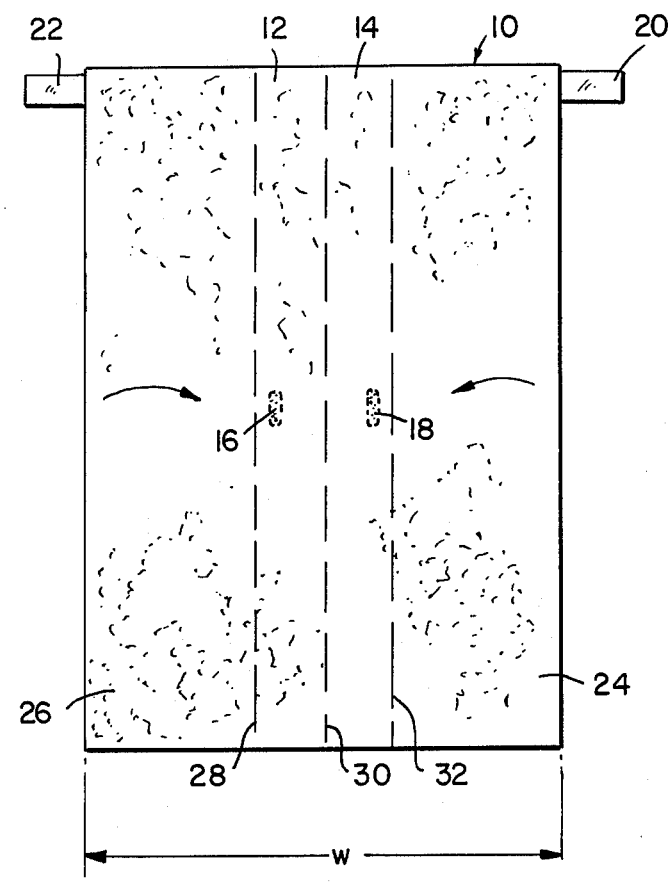
FIG. 1 is a plan view of the diaper in the completely opened position.

With continued reference to the accompanying drawing wherein like reference numerals designate similar parts throughout the views reference numeral 10 is used to generally designate a disposable diaper constructed in accordance with the invention. The diaper is divided into four longitudinal section 12, 14, 24 and 26 by three substantially parallel longitudinal folds 28, 30 and 32. The combined width of longitudinal sections 12 and 14, referred to herein as panels, is approximately from ¼ to ½ the total width W of the diaper. Panels 12 and 14 are approximately equal in width as are flap members 24 and 26. Panels 12 and 14 are provided with adhesive spots 16 and 18 occupying a portion of the width of the panels. However, the adhesive spots 16 and 18 can be sufficiently large to occupy substantially the entire width of panels 12 and 14 to permit a wider degree of diaper adjustment when applied to the infant. The adhesive spots are preferably located substantially centrally longitudinally to provide a better fit. However, minor variation in this regard is permitted to accomplish specific purposes.

Longitudinal sections 24 and 26, hereinafter referred to as flap portions, are adjacent each of panels 12 and 14 and in abutting contact therewith. The combined width of the flap portions is about one-half to three-fourths the total width "w" of the diaper. Adhesive tabs 20 and 22 can be suitably attached to the back sheet of diaper 10 in known manner to extend beyond the longitudinal edges of the diaper to provide fastener means for closing the diaper about the infant when applied.

Figure 2:
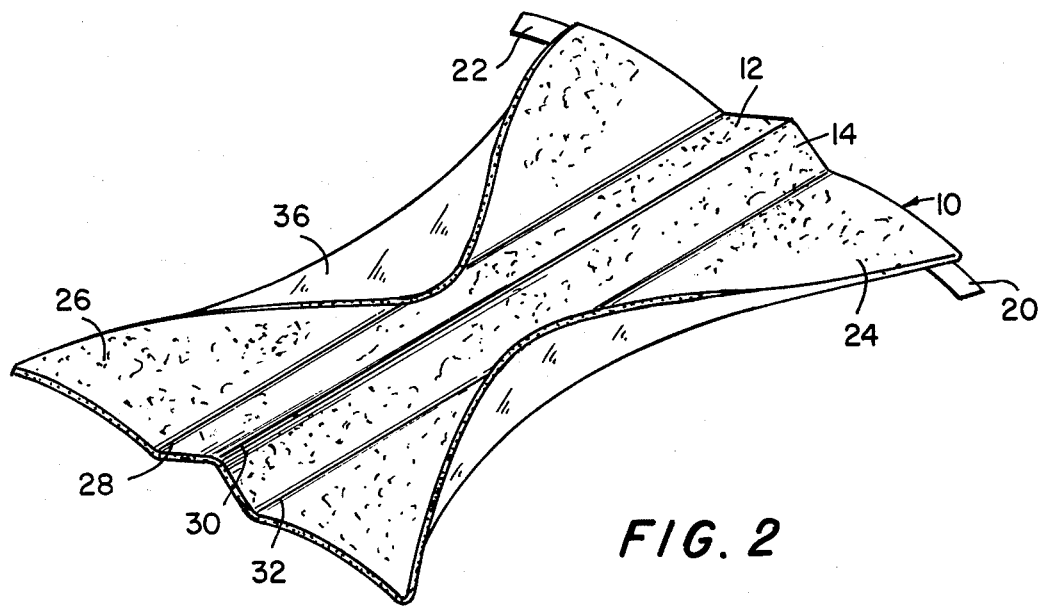
FIG. 2 is a perspective view illustrating the diaper in the folded position for application for the infant.

FIG. 2 illustrates the folded configuration of a diaper constructed in accordance with the invention. Prior to application to the infant, the longitudinal edges of the diaper are folded back upon the top or face sheet and secured thereto by the adhesive spots 16 and 18. The diaper thus has an "Hour glass" or "M" type configuration. In this configuration, the corners of the diaper lie substantially flat. Adhesive spots 16 and 18 may extend substantially the entire width of panels 12 and 14 to afford greater means for achieving a close comfortable fit. Thus, the width of the diaper in the crotch portion can be varied as desired by merely increasing or decreasing, the width of the folded-over flap portions. In this manner, means are provided for enabling adjustment of the diaper dimensions to the particular contour requirements of the infant and thus a "custom fit" can be readily achieved.

Providing the diaper with only three longitudinal folds as illustrated is essential. Longitudinal fold 30 provided a center line about which the internal stresses of the diaper assembly are essentially balanced. Thus, the diaper has little if any tendency to buckle or otherwise become structurally untoward in the pre-folded or folded condition. This effectively expedites manipulation of the diaper with only a single hand. For optimum results the total width of panels 12 and 14 comprise about one-fourth to one-half the total width of diaper 10, for structural stability and improved performance characteristics.

The "hour glass" configuration provides when the diaper is applied to the infant a narrowed portion in the crotch area having increased thickness due to the overlying, folded over flap portions. The narrowed portion of the diaper gives enhanced infant comfort and improved appearance while the increased thickness gives to increased absorptive capacity. The "M" configuration minimizes the total area of the water pervious face layer covered by the water impervious back sheet 36. The absorptive capacity and efficiency of the diaper are enhanced significantly, particularly compared to conventional "wing fold" diapers. Since the diaper can be easily hand-shaped to fit snugly around the legs and trunk of the infant, retention of waste fluids is more effective, allowing greater opportunity for the waste fluid to be absorbed by the middle absorbent layer. In this manner, dripping of excess fluid is minimized if not eliminated.

The layers comprising the diaper assembly can be prepared from materials well known in the art. The back sheet comprises a hydrophobic water impervious material made of a thin flexible plastic material such as polyethylene, polypropylene, polyvinyl chloride and the like. The middle layer which is the absorbent pad layer, can comprise cellulose wadding sandwiched between layers made of porous paper or non-woven web. Alternatively, the absorbent layer may simply comprise multiple plies of absorbent material such as cellulose wadding. The face sheet which contacts the infant when applied comprises water pervious hydrophobic material such as hydrophobic paper. The aforedescribed materials are described in detail in a variety of publications. Any of these materials are suitable for use herein.

A latitude of modification, substitution and change is intended in the foregoing disclosure, and in some instances, some features of the present invention may be employed without a corresponding use of other features.

What is claimed is:

1. A disposable diaper substantially rectangular in shape and having only four longitudinal sections, said diaper comprising in order, a water pervious layer, an absorbent pad layer and a water impervious layer, two of said sections being a pair of abutting, substantially centrally located longitudinal panels defined by three substantially parallel longitudinal folds extending the length of said diaper, said panels being of approximately equal width and the combined width of said panels being from one-fourth to one-half the width of said diaper, a flap portion adjacent each of said panels, said adhesive means on each of said panels approximately centrally located longitudinally thereof, said adhesive means being deposits of adhesive extending less than the width of each of said panels, said flap portions overlying said deposits of adhesive and only partially overlying said water pervious layer and secured thereto by said deposits of adhesive to form an hour glass configuration, with the corners of the diaper lying flat, adhesive tab means attached to said water impervious layer at least one corner of said diaper, said water impervious layer comprising a thin, flexible plastic material of polyethylene, polypropylene or polyvinyl chloride, said absorbent pad layer being cellulose wadding, said water pervious layer being hydrophobic paper.

* * * * *